United States Patent
Gottschalk-Gaudig et al.

(10) Patent No.: US 7,276,615 B2
(45) Date of Patent: Oct. 2, 2007

(54) ORGANOFUNCTIONAL SURFACE-MODIFIED METAL OXIDES

(75) Inventors: Torsten Gottschalk-Gaudig, Burghausen (DE); Herbert Barthel, Emmerting (DE); Juergen Pfeiffer, Burghausen (DE)

(73) Assignee: Wacker Chemie AG, Munich (DE)

( * ) Notice: Subject to any disclaimer, the term of this patent is extended or adjusted under 35 U.S.C. 154(b) by 491 days.

(21) Appl. No.: 10/834,663

(22) Filed: Apr. 29, 2004

(65) Prior Publication Data

US 2004/0220419 A1 Nov. 4, 2004

(30) Foreign Application Priority Data

May 2, 2003 (DE) .................. 103 19 937

(51) Int. Cl.
*C07F 7/02* (2006.01)
*C01B 13/00* (2006.01)

(52) U.S. Cl. ...................... 556/10; 423/579

(58) Field of Classification Search ............... 556/10; 423/579

See application file for complete search history.

(56) References Cited

U.S. PATENT DOCUMENTS 6,197,863 B1 3/2001 Eck et al.

FOREIGN PATENT DOCUMENTS

EP 0896029 5/2000

OTHER PUBLICATIONS

Chemical Abstract AN 1988:131899 corresp. to Wu, Xugin et al.
Chemical Abstract AN 1981:498753 corresp. to Morozova, E.M. et al.
Chemical Abstract AN 1981:85024 corresp. to Morozova, E.M. et al.
Chemical Abstract AN 1980:23004 corresp. to Schulz, D. et al.
Chemical Abstract AN 1966:404543 corresp. to Tertykh, V.A. et al.
English Derwent Abstract AN 1999-122267 [11] corres. to EP 0896029.

*Primary Examiner*—Porfirio Nazario-Gonzalez
(74) *Attorney, Agent, or Firm*—Brooks Kushman P.C.

(57) ABSTRACT

A process for preparing a metal oxide having groups of the general formula I $$-O_{1+n}-SiR^1_{2-n}-CH_2-Y \qquad (I)$$

which involves reacting a solid having OH groups on the surface with silanes of the general formula II $$RO_{1+n}-SiR^1_{2-n}-CH_2-Y \qquad (II)$$

where
Y is a functional group $-NR^x_2$, $-OC(O)C(R)=CH_2$, -halo, or -NCO. The reaction takes place rapidly and at reasonable temperatures and avoids production of significant quantities of decomposition products or byproducts, providing a metal oxide with a high proportion of Y functional groups.

15 Claims, No Drawings

ORGANOFUNCTIONAL SURFACE-MODIFIED METAL OXIDES

BACKGROUND OF THE INVENTION

1. Field of the Invention

The invention relates to a process for preparing organofunctionalized solids, particularly organofunctionalized metal oxides, and to solids and metal oxides prepared by the process.

2. Background Art

Surface modification of solids, whether they be pulverulent or mass (bulk) solids, is frequently confronted by the problem that the surface modification is not permanent, i.e., the surface modification agent is not sufficiently anchored to the surface and, therefore, can become detached and washed away by solvent, the surrounding medium, or the surrounding matrix. This problem can be overcome by obtaining a firm chemical attachment involving the formation of chemical bonds, as has been disclosed in EP 896029 B1, for example. But the latter approach then has the disadvantage that the known processes necessitate high temperatures and long reaction times, which in the case in particular of modifying agents that carry reactive organic groups such as methacrylate, epoxy or isocyanate groups can lead to decomposition reactions, and thus an unwanted reduction in the amount of functional groups and to the formation of reaction byproducts which impair the quality of the modified metal oxides, particularly those used as filler.

Reaction byproducts and a loss of functional groups are especially disadvantageous when the solid is surface-treated with the aim of improving its adhesion or crosslinking with the surrounding medium, since such byproducts can alter the adhesion or crosslinking uncontrollably and since crosslinking reactions are sensitively dependent on precise compliance with the stoichiometry of the reactive groups. Reaction byproducts are also particularly disadvantageous when the pulverulent solid is used as a rheological additive in liquid media such as polymers, resins, or resin solutions, since such reaction byproducts can alter the rheology uncontrollably. Reaction byproducts are further particularly disadvantageous when the pulverulent solid is used as a free-flow aid and triboelectric charge control agent in pulverulent systems such as toners, developers, powder coating materials or coating systems, since such reaction byproducts may alter the free flow and triboelectric effects unpredictably.

The addition of Lewis acid or Lewis base catalysts to accelerate the reaction of silica with alkoxysilanes and to improve the reaction yield of silica with alkoxysilanes is known. It has the disadvantage, however, that the catalysts, although they accelerate the binding reaction of the modifying reagents, also frequently catalyze the decomposition reactions of the functional groups.

SUMMARY OF THE INVENTION

It was an object of the invention to provide a surface-modified solids which do not have the disadvantages of the prior art. These and other objects have been achieved by surface modification with specific silanes having reactive functional groups bonded to Si through the intermediary of a methylene group. The use of a methylene group in place of a more conventional higher alkylene group surprisingly provides a marked increase in reactivity of the silane with the metal oxide substrate, lowering the amounts of byproducts and maintaining the functionality provided by the functional group.

DETAILED DESCRIPTION OF THE PREFERRED EMBODIMENT(S)

The invention provides a process for preparing a metal oxide having groups of the general formula I

  (I)

which involves reacting a solid having OH groups on the surface with silanes of the general formula II

  (II)

R is a C—O bonded $C_1$-$C_{15}$ hydrocarbon radical, preferably a $C_1$-$C_8$ hydrocarbon radical, more preferably a $C_1$-$C_3$ hydrocarbon radical, or an acetyl radical, $R^1$ is a hydrogen atom or an Si—C bonded $C_1$-$C_{20}$ hydrocarbon radical unsubstituted or substituted by —CN, —NCO, —NR$^x_2$, —COOH, —COOR$^x$, -halo, -acryloyl, -epoxy, —SH, —OH or —CONR$^x_2$, preferably a $C_1$-$C_8$ hydrocarbon radical, more preferably a $C_1$-$C_3$ hydrocarbon radical, or aryl radical, or $C_1$-$C_{15}$ hydrocarbon or "hydrocarbonoxy" radical, preferably a $C_1$-$C_8$ hydrocarbonoxy radical, more preferably a $C_1$-$C_4$ hydrocarbonoxy radical, in each of which one or more nonadjacent methylene units may have been replaced by groups —O—, —CO—, —COO—, —OCO—, or —OCOO—, —S— or —NR$^x$— and in which one or more nonadjacent methine units may have been replaced by groups —N=, —N=N— or —P=, each $R^1$ being identical or different, Y is a functional group —NR$^x_2$, —OC(O)C(R)=CH$_2$, where R is H, a $C_1$-$C_{15}$ hydrocarbon radical, preferably a $C_1$-$C_8$ hydrocarbon radical, more preferably a $C_1$-$C_3$ hydrocarbon radical, -halo, —NCO, —NH—C(O)—OR, where R is a $C_1$-$C_{15}$ hydrocarbon radical, preferably a $C_1$-$C_8$ hydrocarbon radical, more preferably a $C_1$-$C_3$ hydrocarbon radical, -glycidyloxy or —SH, or $(R^1O)_2(O)P$—, $R^x$ is a hydrogen atom or $C_1$-$C_{15}$ hydrocarbon radical, preferably a $C_1$-$C_8$ hydrocarbon radical, and more preferably a $C_1$-$C_3$ hydrocarbon radical, or aryl radical, each $R^x$ being identical or different, and n is 0, 1 or 2. It should be noted in the structural formula for silane (II), that the —CH$_2$—Y group is attached directly to Si and not to an $R^1$ moiety, the latter of which are also bonded to Si.

Silanes of the formula II that are used are preferably:

aminomethyldimethylmethoxysilane, aminomethylmethyldimethoxysilane, aminomethyltrimethoxysilane, N-methylaminomethyldimethylmethoxysilane, N-methylaminomethylmethyldimethoxysilane, N-methylaminomethyltrimethoxysilane, N-ethylaminomethyldimethylmethoxysilane, N-ethylaminomethylmethyldimethoxysilane, N-ethylaminomethyltrimethoxysilane, N,N-dimethylaminomethyl-dimethylmethoxysilane, N,N-dimethylaminomethylmethyl-dimethoxysilane, N,N-dimethylaminomethyltrimethoxysilane, N,N-diethylaminomethyldimethylmethoxysilane, N,N-diethylaminomethyl-methyldimethoxysilane, N,N-diethylaminomethyltrimethoxysilane, N,N-dipropylaminomethyldimethylmethoxysilane, N,N-dipropylaminomethyl-methyltrimethoxysilane, N,N-dipropylaminomethyltrimethoxysilane, N,N-methylethylaminomethyldimethylmethoxysilane, N,N-methylethylaminomethyl-methyldimethoxysilane, N,N-methylethylaminomethyltrimethoxysilane, anilinomethyldimethylmethoxysilane, anilinomethylyldimethoxysilane, anilinomethyltrimethoxysilane, morpholinomethyldimethylmethoxysilane, morpholinomethylmethyldimethoxysilane, morpholinomethyltrimethoxysilane, N,N,N-trimethylammoniomethyldimethylmethoxysilane, N,N,N-trimethylammoniomethylmethyldimethoxysilane, N,N,N-trimethylammoniomethyltrimethoxysilane, N,N,N-triethylammoniomethyldimethylmethoxysilane, N,N,N-triethylammoniomethylmethyldimethoxysilane, N,N,N-triethylammoniomethyltrimethoxysilane, acryloyloxymethyldimethylmethoxysilane, acryloyloxymethylmethyldimethoxysilane, acryloyloxymethyltrimethoxysilane, methacryloyloxymethyl-dimethylmethoxysilane, methacryloyloxymethyl-methyldimethoxysilane, methacryloyloxymethyltrimethoxysilane, chloromethyldimethylmethoxysilane, chloromethylmethyldimethoxysilane, chloromethyltrimethoxysilane, isocyanatomethyldimethylmethoxysilane, isocyanatomethylmethyldimethoxysilane, isocyanatomethyltrimethoxysilane, methylcarbamatomethyl-dimethylmethoxysilane, methylcarbamatomethyl-methyldimethoxysilane, methylcarbamatomethyltrimethoxysilane, mercaptomethyldimethylmethoxysilane, mercaptomethylmethyldimethoxysilane, mercaptomethyltrimethoxysilane, glycidyloxymethyldimethylmethoxysilane, glycidyloxymethylmethyldimethoxysilane, glycidyloxymethyltrimethoxysilane, dimethoxyphosphitomethyldimethylmethoxysilane, dimethoxyphosphitomethyl-methyldimethoxysilane, dimethoxyphosphitomethyltrimethoxysilane, diethoxyphosphitomethyldimethylmethoxysilane, diethoxyphosphitomethyl-methyldimethoxysilane, diethoxyphosphitomethyltrimethoxysilane, diphenoxyphosphitomethyldimethylmethoxysilane, diphenoxyphosphitomethyl-methyldimethoxysilane, diphenoxyphosphitomethyltrimethoxysilane, aminomethyldimethylethoxysilane, aminomethylmethyldiethoxysilane, aminomethyltriethoxysilane, N-methylaminomethyldimethylethoxysilane, N-methylaminomethylmethyldiethoxysilane, N-methylaminomethyltriethoxysilane, N-ethylaminomethyldimethylethoxysilane, N-ethylaminomethylmethyldiethoxysilane, N-ethylaminomethyl-triethoxysilane, N,N-dimethylaminomethyldimethylethoxysilane, N,N-dimethylaminomethylmethyldiethoxysilane, N,N-dimethylaminomethyltriethoxysilane, N,N-diethylaminomethyldimethylethoxysilane, N,N-diethylaminomethylmethyldiethoxysilane, N,N-diethylaminomethyltriethoxysilane, N,N-dipropylaminomethyldimethylethoxysilane, N,N-dipropylaminomethylmethyltriethoxysilane, N,N-dipropylaminomethyltriethoxysilane, N,N-methylethylaminomethyldimethylethoxysilane, N,N-methylethylaminomethylmethyldiethoxysilane, N,N-methylethylaminomethyltriethoxysilane, anilinomethyldimethylethoxysilane, anilinomethylmethyldiethoxysilane, anilinomethyltriethoxysilane, morpholinomethyldimethylethoxysilane, morpholinomethylmethyldiethoxysilane, morpholinomethyl-triethoxysilane, N,N,N-trimethylammoniomethyldimethylethoxysilane, N,N,N-trimethylammoniomethylmethyldiethoxysilane, N,N,N-trimethylammoniomethyltriethoxysilane, N,N,N-triethylammoniomethyldimethylethoxysilane, N,N,N-triethylammoniomethylmethyldiethoxysilane, N,N,N-triethylammoniomethyltriethoxysilane, acryloyloxymethyldimethylethoxysilane,acryloyloxymethy(-methyl-methyldiethoxysilane, acryloyloxymethyltriethoxysilane, methacryloyloxymethyldimethylethoxysilane, methacryloyloxymethylmethyldiethoxysilane, methacryloyloxymethyltriethoxysilane, chloromethyldimethylethoxysilane, chloromethylmethyldiethoxysilane, chloromethyltriethoxysilane, isocyanatomethyldimethylethoxysilane, isocyanatomethylmethyldiethoxysilane, isocyanatomethyltriethoxysilane, methylcarbamatomethyl-dimethylethoxysilane, methylcarbamatomethylmethyldiethoxysilane, methylcarbamatomethyltriethoxysilane, mercaptomethyldimethylethoxysilane, mercaptomethylmethyldiethoxysilane, mercaptomethyltriethoxysilane, glycidyloxymethyldimethylethoxysilane, glycidyloxymethylmethyldiethoxysilane, glycidyloxymethyltriethoxysilane, dimethoxyphosphitomethyldimethylethoxysilane, dimethoxyphosphitomethyl-methyldiethoxysilane, dimethoxyphosphitomethyltriethoxysilane, diethoxyphosphitomethyldimethylethoxysilane, diethoxyphosphitomethyl-methyldiethoxysilane, diethoxyphosphitomethyltriethoxysilane, diphenoxyphosphitomethyldimethylethoxysilane, diphenoxyphosphitomethyl-methyldiethoxysilane, diphenoxyphosphitomethyltriethoxysilane, aminomethyldimethylacetoxysilane, aminomethylmethyldiacetoxysilane, aminomethyltriacetoxysilane, N-methylaminomethyldimethylacetoxysilane, N-methylaminomethylmethyldiacetoxysilane, N-methylaminomethyltriacetoxysilane, N-ethylaminomethyldimethyl-acetoxysilane, N-ethylaminomethylmethyldiacetoxysilane, N-ethylaminomethyltriacetoxysilane, N,N-dimethylaminomethyldimethyl-acetoxysilane, N,N-dimethylaminomethylmethyldiacetoxysilane, N,N-dimethylaminomethyltriacetoxysilane, N,N-diethylaminomethyldimethylacetoxysilane, N,N-diethylaminomethylmethyldiacetoxysilane, N,N-diethylaminomethyltriacetoxysilane, N,N-dipropylaninomethyldimethylacetoxysilane, N,N-dipropylaminomethylmethyltriacetoxysilane, N,N-dipropylaminomethyltriacetoxysilane, N,N-methylethylaminomethyldimethylacetoxysilane, N,N-methylethylaminomethylmethyldiacetoxysilane, N,N-methylethylaminomethyltriacetoxysilane, anilinomethyldimethylacetoxysilane, anilinomethylmethyldiacetoxysilane, anilinomethyltriacetoxysilane, morpholinomethyldimethylacetoxysilane, morpholinomethylmethyldiacetoxysilane, morpholinomethyl-triacetoxysilane, N,N,N-trimethylammoniomethyldimethylacetoxysilane, N,N,N-trimethylammoniomethylmethyldiacetoxysilane, N,N,N-trimethylammoniomethyltriacetoxysilane, N,N,N-triethylammoniomethyldimethylacetoxysilane, N,N,N-triethylammoniomethylmethyldiacetoxysilane, N,N,N-triethylammoniomethyltriacetoxysilane, acryloyloxymethyldimethylacetoxysilane, acryloyloxymethylmethyldiacetoxysilane, acryloyloxymethyltriacetoxysilane, methacryloyloxymethyl-dimethylacetoxysilane, methacryloyloxymethylmethyldiacetoxysilane, methacryloyloxymethyltriacetoxysilane, chloromethyldimethylacetoxysilane, chloromethylmethyldiacetoxysilane, chloromethyltriacetoxysilane, isocyanatomethyldimethylacetoxysilane, isocyanatomethylmethyldiacetoxysilane, isocyanatomethyltriacetoxysilane, methylcarbamatomethyldimethyl-acetoxysilane, methylcarbamatomethylmethyldiacetoxysilane, methylcarbamatomethyltriacetoxysilane, mercaptomethyldimethylacetoxysilane, mercaptomethylmethyldiacetoxysilane, mercaptomethyltriacetoxysilane, glycidyloxymethyldimethylacetoxysilane, glycidyloxymethylmethyldiacetoxysilane, glycidyloxymethyltriacetoxysilane, dimethoxyphosphitomethyldimethylacetoxysilane, dimethoxyphosphitomethyl-methyldiacetoxysilane, dimethoxyphosphitomethyltriacetoxysilane, diethoxyphosphitomethyldimethylacetoxysilane, diethoxyphosphitomethyl-methyldiacetoxysilane, diethoxyphosphitomethyltriacetoxysilane, diphenoxyphosphitomethyldimethylacetoxysilane, diphenoxyphosphitomethyl-methyldiacetoxysilane, and dimethoxyphosphitomethyltriacetoxysilane.

In the case of silanes of the formula II with condensation-catalyzing groups Y which are amino-, mercapto-, isocyanato-, and carbamato-, preference is given to mono-, di-, and trialkoxysilanes RO—SiR$^1{}_2$—CH$_2$—Y, (RO)$_2$SiR$^1$—CH$_2$—Y, and (RO)$_3$Si—CH$_2$—Y with alkyl radicals R being independently selected from methyl radicals, ethyl radicals, propyl radicals such as the iso- or n-propyl radical, butyl radicals such as the t- or n-butyl radical, pentyl radicals such as the neo-, the iso- or n-pentyl radicals, hexyl radicals such as the n-hexyl radical, heptyl radicals such as the n-heptyl radical, octyl radicals such as the 2-ethylhexyl or n-octyl radicals, decyl radicals such as the n-decyl radical, dodecyl radicals such as the n-dodecyl radical, hexadecyl radicals such as the n-hexadecyl radical, octadecyl radicals such as the n-octadecyl radical, or the acetoxy radical, with particular preference given to monoalkoxysilanes RO—SiR$^1{}_2$—CH$_2$—Y with radicals R being methyl radicals.

In the case of silanes of the formula II with noncondensation-catalyzing groups Y, for example halo-, acrylate-, alkylacrylate-, and glycidyloxy-, preference is given to mono-, di-, and trialkoxysilanes RO—SiR$^1{}_2$—CH$_2$—Y, (RO)$_2$SiR$^1$—CH$_2$—Y, and (RO)$_3$Si—CH$_2$—Y with alkyl radicals R as defined above.

In the case of silanes of the formula II with noncondensation-catalyzing groups Y being halo-, acrylate-, alkylacrylate-, and glycidyloxy-, in one preferred embodiment, preference is given to monoalkoxysilanes RO—SiR$^1{}_2$—CH$_2$—Y (n=2) with the alkyl radicals R as defined above, with particular preference given to monoalkoxysilanes RO—SiR$^1{}_2$—CH$_2$—Y (n=2) with the alkyl radicals R being a methyl radical or acetoxy radical. Monoalkoxysilanes RO—SiR$^1{}_2$—CH$_2$—Y produce a well-defined brushlike surface modification.

In another preferred embodiment, preference is given to dialkoxysilanes RO$_2$—SiR$^1$—CH$_2$—Y (n=1) with the alkyl radicals R as defined above with particular preference given to dialkoxysilanes RO$_2$—SiR$^1$—CH$_2$—Y (n=1) with the alkyl radical R being a methyl radical or acetoxy radical. Dialkoxysilanes RO$_2$—SiR$^1$—CH$_2$—Y produce a surface modification with cyclic and loop structures.

In a further embodiment, preference is given to trialkoxysilanes (RO)$_3$Si—CH$_2$—Y (n=0) with the alkyl radicals R as defined above, with particular preference to trialkoxysilanes (RO)$_3$Si—CH$_2$—Y (n=0) wherein the alkyl radicals R are methyl radicals or acetoxy radicals. Trialkoxysilanes (RO)$_3$Si—CH$_2$—Y produce a surface modification with resinous structures.

Examples of R$^1$ are preferably the following: alkyl radicals such as the methyl radical, ethyl radical, propyl radicals such as the iso- or n-propyl radicals, butyl radicals such as the t- or n-butyl radicals, pentyl radicals such as the neo-, the iso- or n-pentyl radicals, hexyl radicals such as the n-hexyl radical, heptyl radicals such as the n-heptyl radical, octyl radicals such as the 2-ethylhexyl or n-octyl radicals, decyl radicals such as the n-decyl radical, dodecyl radicals such as the n-dodecyl radical, hexadecyl radicals such as the n-hexadecyl radical, octadecyl radicals such as the n-octadecyl radical, aryl radicals such as the phenyl, biphenylyl or naphthyl radicals, alkylaryl radicals such as the benzyl, ethylphenyl, tolyl, or the xylyl radical. More preferably, R$^1$ are selected from methyl radicals, ethyl radicals, or propyl radicals such as the iso- or n-propyl radical, and with particular preference, the methyl radical.

Examples of Y are preferably the following: a primary amine radical —NH$_2$, secondary amine radicals such as the N-monomethyl, N-monoethyl, N-monopropyl, N-monobutyl or anilino radicals, tertiary amine radicals such as the N,N-dimethyl, N,N-diethyl, N,N-dipropyl, N,N-dibutyl, N,N-methylethyl, N,N-methylpropyl, N,N-ethylpropyl or N,N-methylphenyl radicals, or the morpholino radical, the pyrrolyl radical, the indolyl radical, the pyrazolyl, imidazolyl or piperidyl radical, tertiary ammonium radicals such as the N,N,N-trimethylammonium, N,N,N-triethylammonium, or N,N,N-tripropylammonium radicals, the acrylate radical, alkylacrylate radicals such as the methacrylate, ethylacrylate, propylacrylate, butylacrylate or phenylacrylate radicals, halo radicals such as the chloro, bromo or iodo radicals, isocyanato and carbamato radicals, the thiol radical, the glycidyloxy radical, and phosphonato radicals such as the dimethoxy-, the diethoxy- or the diphenoxyphosphonato radical.

Silanes of the general formula II wherein the reactive group Y is attached through a CH$_2$ spacer to the Si atom have much higher reactivities with respect to condensation reactions on the Si atom than the prior art silanes in which the reactive group Y is attached through a C$_3$H$_6$ spacer to the Si atom. Since the reaction of solids with silanes of the general formula II can be conducted under milder conditions, i.e., at lower temperatures and in shorter reaction times, the surface modification proceeds substantially without decomposition reactions and without the attendant loss of reactive groups and formation of reaction byproducts.

For surface modification, the silanes of the general formula II can be used alone or in any desired mixtures with organosiloxanes composed of units of the formula $(R^3{}_3SiO_{1/2})$, and/or $(R^3{}_2SiO_{2/2})$, and/or $(R^3SiO_{3/2})$, the number of these units in an organosiloxane being at least 2, and it being possible for R$^3$ to be an optionally mono- or polyunsaturated, monovalent, optionally halogenated hydrocarbon radical having preferably 1 to 18 carbon atoms, or to be halogen, a nitrogen radical, OR$^4$, OCOR$^4$, O(CH$_2$)$_x$OR$^4$, where R$^4$ is hydrogen or a monovalent hydrocarbon radical having 1 to 18 carbon atoms, and where the radicals R$^3$ may be identical or different. The organosiloxanes are preferably liquid at surface-covering temperatures.

Examples of R$^3$ are the following: alkyl radicals such as the methyl and ethyl radicals, propyl radicals such as the iso- or the n-propyl radical, butyl radicals such as the t- or n-butyl radical, pentyl radicals such as the neo-, the iso- or the n-pentyl radicals, hexyl radicals such as the n-hexyl radical, heptyl radicals such as the n-heptyl radical, octyl radicals such as the 2-ethylhexyl or the n-octyl radical, decyl radicals such as the n-decyl radical, dodecyl radicals such as the n-dodecyl radical, hexadecyl radicals such as the n-hexadecyl radical, octadecyl radicals such as the n-octadecyl radical, alkenyl radicals such as the vinyl, the 2-allyl or the 5-hexenyl radicals, aryl radicals such as the phenyl, the biphenylyl or naphthyl radicals, alkylaryl radicals such as benzyl, ethylphenyl, tolyl or the xylyl radicals, halogenated alkyl radicals such as the 3-chloropropyl, the 3,3,3-trifluoropropyl or the perfluorohexylethyl radicals, and halogenated aryl radicals such as the chlorophenyl or chlorobenzyl radical.

Preferred examples of $R^3$ are the methyl radical, the octyl radical, and the vinyl radical. The methyl radical is particularly preferred.

Examples of organosiloxanes are linear or cyclic dialkylsiloxanes having an average number of dialkylsiloxy units of greater than 2, preferably greater than 10. The dialkylsiloxanes are preferably dimethylsiloxanes.

Examples of linear polydimethylsiloxanes are those having the following end groups: trimethylsiloxy, dimethylhydroxysiloxy, dimethylchlorosiloxy, methyldichlorosiloxy, dimethylmethoxysiloxy, methyldimethoxysiloxy, dimethylethoxysiloxy, methyldiethoxysiloxy, dimethylacetoxysiloxy, and methyldiacetoxysiloxy; trimethylsiloxy and dimethylhydroxysiloxy end groups are particularly preferred. The end groups can be identical or different.

The process of the invention uses a solid which is to be surface modified. The solid used, with OH groups on the surface, can be any solid: for example, an organic solid such as cellulose, a metal with an oxidized surface, such as silicon, aluminum, or iron, a mineral glass, such as quartz glass or window glass, or a metal oxide.

The base product (starting product) used for the surface modification is preferably a solid having an average particle size of <1000 μm, in particular an average primary particle size of from 5 to 100 nm. These primary particles may not exist in isolation but instead may be constituents of larger aggregates and agglomerates.

Preferred solids are metal oxides. Preferably the metal oxide has a specific surface area of preferably from 0.1 to 1000 m²/g (measured by the BET method in accordance with DIN 66131 and 66132), more preferably from 10 to 500 m²/g.

The metal oxide may comprise aggregates (as defined in DIN 53206) preferably in a range of diameters, from 100 to 1000 nm, with the metal oxide comprising agglomerates (as defined in DIN 53206) which are composed of aggregates and which as a function of the external shear load (e.g., as a result of the measuring conditions) may have sizes of from 1 to 1000 μm.

In order that it can be handled industrially, the metal oxide is preferably an oxide with a covalent bonding component in the metal-oxygen bond, preferably an oxide in the solid aggregate state of the main group and transition group elements, such as those of main group 3, for example boron, aluminum, gallium or indium oxide, or of main group 4, such as silicon dioxide, germanium dioxide, tin oxide or dioxide, lead oxide or dioxide, or an oxide of transition group 4, such as titanium dioxide, zirconium oxide, or hafnium oxide. Other examples are stable oxides of nickel, of cobalt, of iron, of manganese, of chromium or of vanadium.

Particular preference is given to aluminum(III), titanium (IV), and silicon(IV) oxides, such as silica gels or silicas prepared wet-chemically, for example by precipitation, or aluminum oxides, titanium dioxides or silicon dioxides prepared in elevated-temperature operations, for example pyrogenically prepared aluminum oxides, titanium dioxides or silicon dioxides, or silica.

Other solids are silicates, aluminates or titanates, or aluminum phyllosilicates, for example bentonites such as montmorillonites, or smectites or hectorites. Other solids that can be used are carbon blacks such as lamp blacks, oven blacks, so-called furnace blacks, or carbon blacks which can be used as a colorant or as a reinforcing filler or as a rheological additive.

Particular preference is given to pyrogenic silica which is prepared in a flame reaction from organosilicon compounds, e.g., from silicon tetrachloride, or from methyldichlorosilane, hydrotrichlorosilane, hydromethyldichlorosilane, or other methylchlorosilanes or alkylchlorosilanes, as they are or in admixture with hydrocarbons, or any desired volatilizable or sprayable mixtures of organosilicon compounds, as mentioned, and hydrocarbons, e.g., in an oxyhydrogen flame, or else in a carbon monoxide/oxygen flame. The silica can be prepared with or without the optional further addition of water, in the purification step, for example. It is preferred not to add water. Any desired mixtures of the solids stated may be used for the surface modification.

The pyrogenic silica preferably has a fractal surface dimension of less than or equal to 2.3, more preferably less than or equal to 2.1, and in particular from 1.95 to 2.05, the fractal surface dimension, $D_S$, being defined here as follows: particle surface area A is proportional to particle radius R to the power of $D_s$.

The silica preferably has a fractal mass dimension $D_m$ of less than or equal to 2.8, more preferably less than or equal to 2.7, and most preferably from 2.4 to 2.6. The fractal mass dimension, $D_m$, is defined here as follows: particle mass M is proportional to particle radius R to the power of $D_m$.

Preferably the silica has a density of available surface silanol groups SiOH available for chemical reaction at the surface, of less than 2.5 SiOH/nm², preferably less than 2.1 SiOH/nm², more preferably less than 2 SiOH/nm², and most preferably from 1.7 to 1.9 SiOH/nm².

It is possible to use silicas prepared wet-chemically or at a high temperature (>1000° C.). Particular preference is given to silicas prepared pyrogenically. It is also possible to use hydrophilic metal oxides which come freshly prepared direct from the burner, have been stored, or have already been packaged in a commercially customary fashion. It is additionally possible to use hydrophobicized metal oxides or silicas, e.g., commercially customary silicas. Both uncompacted silicas, with bulk densities of preferably <60 g/l, and compacted silicas, with bulk densities of preferably >60 g/l, can be used. Mixtures of different metal oxides or silicas can also be used for example, mixtures of metal oxides or silicas differing in BET surface area, or mixtures of metal oxides differing in degree of hydrophobicization or degree of silylation.

Processes for Preparing the Metal Oxide:

The surface modified metal oxide of the invention can be prepared in continuous or batchwise processes; the process for silylation may be composed of one or more steps. With preference, the silylated metal oxide is prepared by means of a process in which the preparation takes place in separate steps: (A) first, preparation of the hydrophilic metal oxide, then (B) silylation of the metal oxide with (1) loading of the hydrophilic metal oxide with a silane of the general formula II, (2) reaction of the hydrophilic metal oxide with the silane of the general formula II, and (3) purification of the metal oxide to remove excess silane with the general formula II.

The surface treatment is preferably conducted in an atmosphere which does not lead to oxidation of the silylated metal oxide: that is, preferably in an atmosphere containing less than 10% by volume oxygen, more preferably less than 2.5% by volume, the best results being obtained at less than 1% by volume oxygen.

Loading, reaction, and purification can be carried out as a batchwise or continuous operation. For technical reasons preference is given to a continuous reaction regime.

Loading preferably takes place at temperatures of −30 to 250° C., preferably 20-150° C., more preferably 20-80° C.; the covering step is preferably cooled to 30-50° C. The residence time is generally 1 min-24 h, preferably from 15 min to 240 min, and with particular preference, for reasons of the space/time yield, from 15 min to 90 min.

The pressure at the loading stage ranges from a slight underpressure, for example down to 0.2 bar, to an overpressure of 100 bar or higher, preference being given on technical grounds to normal pressure, that is, unpressurized operation with respect to external/atmospheric pressure.

The silane of the general formula II is preferably added as a liquid and in particular is mixed into pulverulent metal oxide. This is preferably done by means of nozzle techniques, or comparable techniques, for example effective spraying techniques such as spraying in 1-fluid nozzles under pressure, preferably from 5 to 20 bar, spraying in 2-fluid nozzles under pressure, preferably gas and liquid, 2 to 20 bar, ultrafine division with atomizers or gas/solid exchange assemblies with movable, rotating or static internals which permit homogeneous distribution of the silane with the pulverulent metal oxide. Preferably the silane of the general formula II is added as an ultrafinely divided aerosol, characterized in that the aerosol has a settling velocity of 0.1 to 20 cm/s and a droplet size with an aerodynamic particle radius of 5 to 25 μm.

Preferably the loading of the metal oxide and the reaction with the silane of the general formula II take place under mechanical or gasborne fluidization. Mechanical fluidization is particularly preferred. Gasborne fluidization can be by means of all inert gases which do not react substantially with the silane of the general formula II, with the metal oxide or with the silylated metal oxide, that is, which do not lead to significant side reactions, degradation reactions, oxidation events or flame or explosion phenomena. Preferred gases include $N_2$, Ar, other noble gases, $CO_2$, etc. The fluidizing gases are supplied preferably at superficial gas velocities of from 0.05 to 5 cm/s, and with particular preference from 0.5 to 2.5 cm/s.

Particular preference is given to mechanical fluidization, which takes place without additional employment of gas beyond that used for inertization, by means of paddle stirrers, anchor stirrers, and other suitable stirring elements. In one particularly preferred embodiment unreacted silane of the general formula II and exhaust gases from the purification step are recycled to the step of loading the metal oxide. The recycling may be partial or complete, accounting preferably for 10 to 90% of the overall volume flow of the gases emerging from the purification step. This takes place in suitably thermostated apparatus.

Recycling preferably takes place in non-condensed phase, i.e., in the form of gas or in the form of vapor. This recycling can take place as mass transport along a pressure equalization or as controlled mass transport with the standard industry gas transport systems such as fans, pumps, and compressed-air membrane pumps. Since it is preferred to recycle the non-condensed phase it may be advisable to heat the recycle lines.

The recycling of the unreacted silane of the general formula II and of the exhaust gases may be situated in this case at between 5 and 100% by weight, based on their total mass, preferably between 30 and 80% by weight. Recycling may amount to between 1 and 200 parts per 100 parts of fresh silane used, preferably from 10 to 30 parts. Recycling of the purification products from the silylation reaction to the loading stage is preferably continuous. The reaction preferably takes place at temperatures of 20 to 200° C., preferably 20 to 160° C., and more preferably 20 to 100° C. The reaction time is generally from 5 min to 48 h, preferably from 10 min to 5 h.

It is optionally possible to add protic solvents such as liquid or vaporizable alcohols or water. Typical alcohols include isopropanol, ethanol, and methanol. It is also possible to add mixtures of the abovementioned protic solvents. It is preferred to add from 1 to 50% by weight of protic solvent, based on the metal oxide, more preferably from 5 to 25% by weight. Water is particularly preferred. Optionally it is possible to add acidic catalysts having an acidic nature in the sense of a Lewis acid or of a Brönsted acid, for example hydrogen chloride, or basic catalysts having a basic nature in the sense of a Lewis base or of a Brönsted base, for example ammonia. They are preferably added in traces, e.g. less than 1000 ppm. It is particularly preferred not to add any catalysts.

Purification generally takes place at a temperature of from 20 to 200° C., preferably from 50° C. to 150° C., and more preferably from 50 to 100° C. The purification step is preferably characterized by agitation, with preference being given particularly to slow agitation and slight mixing. The stirring elements are advantageously set and agitated in such a way that mixing and fluidization occur but not complete vortexing.

The purification step may additionally be characterized by an increased gas input, for example preferably corresponding to a superficial gas velocity of from 0.001 to 10 cm/s, more preferably from 0.01 to 1 cm/s. This can be accomplished employing all inert gases which do not react with the silane of the general formula II, the metal oxide, or the silylated metal oxide, i.e., which do not lead to side reactions, degradation reactions, oxidation events or flame or explosion phenomena. Examples include $N_2$, Ar, other noble gases, $CO_2$, etc.

In addition it is possible and preferably, during the silylation step or following the purification step, to employ methods for the mechanical compaction of the metal oxide, such as press rollers, milling assemblies such as edge runner mills and such as ball mills, continuously or batchwise, compaction by screws or worm mixers, worm compactors, briquetting machines, or compaction by withdrawal of the air or gas present by means of suitable vacuum methods.

Particular preference is given to mechanical compaction during the silylating step, in step (II) of the reaction, by means of press rollers, abovementioned milling assemblies such as ball mills, or compaction by means of screws, worm mixers, worm compactors and/or briquetting machines.

In a further particularly preferred procedure purification is followed by deployment of methods for the mechanical compaction of the metal oxide, such as compaction by suction withdrawal of the air or gas present by means of suitable vacuum methods, or by press rollers, or a combination of both methods.

Additionally it is possible in one particularly preferred procedure, following purification, to employ methods for deagglomerating the metal oxide such milling/classifying devices, including pin-disk mills, hammer mills, opposed-jet mills, or impact mills.

The silane of the general formula II is preferably used in an amount of more than 0.5% by weight based on the weight of the metal oxide, more preferably more than 3% by weight and most preferably, more than 5% by weight.

The invention further provides a metal oxide, preferably a silica, in particular a pyrogenic silica, having a modified surface, the surface being modified with groups of the general formula I.

In the case of silyl radicals of the formula I, mono-, di-, and trisiloxy radicals —O—SiR$^1_2$—CH$_2$—Y, (—O)$_2$SiR$^1$—CH$_2$—Y, and (—O)$_3$Si—CH$_2$—Y with condensation-catalyzing groups Y being amino, mercapto, isocyanato, phosphonato, and/or carbamato groups are preferred, particular preference being given to monosiloxy radicals —O—SiR$^1_2$—CH$_2$—Y.

In the case of silyl radicals of the formula I, mono-, di-, and trisiloxy radicals —O—SiR$^1_2$—CH$_2$—Y, (—O)$_2$SiR$^1$—CH$_2$—Y, and (—O)$_3$Si—CH$_2$—Y, with non-condensation-catalyzing groups Y being halo, acrylate, alkylacrylate, glycidyloxy groups are also preferred, particular preference being given to trisiloxy radicals (—O)$_3$—SiR$^1_2$—CH$_2$—Y.

The invention additionally provides a silica having a modified surface, the surface being modified with groups of the general formula I, the silica having an average primary particle size of less than 100 nm, preferably having an average primary particle size of from 5 to 50 nm, these primary particles existing not in isolation in the silica but instead being constituents of larger aggregates, as defined in accordance with DIN 53206, which have a diameter of from 100 to 1000 nm and constitute agglomerates as defined in accordance with DIN 53206 which, depending on the external shear load, have sizes from 1 to 500 µm, the silica having a specific surface area of from 10 to 400 m$^2$/g measured by the BET method in accordance with DIN 66131 and 66132, the silica having a fractal mass dimension $D_m$ of less than or equal to 2.8, preferably less than or equal to 2.7, more preferably from 2.4 to 2.6, and a surface silanol group SiOH density of less than 1.5 SiOH/nm$^2$, preferably less than 0.5 SiOH/nm$^2$, and more preferably less than 0.25 SiOH/nm$^2$.

The invention further provides a reinforcing filler or rheological additive comprising at least one metal oxide of the invention or at least one silica of the invention.

As an additional characterizing feature, the surface-modified metal oxide generally has a high thickening action in polar systems such as solvent-free polymers and resins, or such as solutions, suspensions, emulsions, and dispersions of organic resins such as polyesters, vinyl esters, epoxy, polyurethane, alkyd resins, etc. in aqueous systems or organic solvents and is therefore suitable as a rheological additive in such systems.

As a further characterizing feature, the surface-modified metal oxide generally has a low thickening action in apolar systems such as noncrosslinked silicone rubber, but at the same time exhibits a high reinforcing effect in the crosslinked silicone rubbers and is therefore outstandingly suitable as a reinforcing filler for silicone rubbers.

As a further characterizing feature the surface-modified metal oxide prevents deposition or caking in pulverulent systems under the effect of moisture, for example, but also does not tend toward reagglomeration, and hence toward unwanted separation, but instead keeps powders flowable and therefore allows mixtures which are stable under load and stable on storage. In this case use is generally made of amounts of metal oxide of 0.1 to 3% by weight, based on the pulverulent system. This applies particularly to use in magnetic and nonmagnetic toners and developers and to charge control agents, e.g., in contactless or electrophotographic printing/reproduction processes, which may be 1-component and 2-component systems. This also applies to pulverulent resins which are used as coating systems.

The invention relates particularly to the use of the metal oxide in systems of low to high polarity as a viscosity-imparting component. This relates to all solvent-free, solvent-containing, water-dilutable, film-forming coating compositions, rubberlike to hard coatings, adhesives, sealing and casting compounds, and other, comparable systems.

The surface modified metal oxides can be used in systems such as epoxy systems, polyurethane (PU) systems, vinyl ester resins, unsaturated polyester resins, water-soluble and water-dispersible resin systems, low-solvent resin systems, called high-solids systems, and solvent-free resins which are applied in powder form as, for example, coating materials. As a rheological additive to these systems the metal oxide provides the requisite viscosity, pseudoplasticity, and thixotropy and provides a yield point which is sufficient for the composition to be able to stand on vertical surfaces.

The metal oxide can be used especially as a theological additive and reinforcing filler in noncrosslinked and crosslinked silicone systems, for example silicone elastomers which are composed of silicone polymers such as polydimethylsiloxanes, fillers, and further additives. These systems can be crosslinked, for example, with peroxides, or crosslinked by way of addition reactions, e.g. by hydrosilylation between olefinic groups and Si-H groups, or by way of condensation reactions between silanol groups such as those reactions which come about on exposure to water.

The metal oxide may further be used as a reinforcing filler, rheological additive, and as an additional crosslinking component in elastomers, in resins, including reactive resins, and in polymers.

The metal oxide may further be used as a Theological additive and reinforcing filler, and as an additional crosslinking component for improving mechanical properties such as impact strength or scratch resistance, of reactive resin systems such as epoxy, polyurethane, vinyl ester, unsaturated polyester or methacrylate resins. This relates to all solvent-free, solvent-containing, water-dilutable, film-forming coating compositions, rubberlike to hard coatings, adhesives, sealing and casting compounds, and other, comparable systems. Typical amounts in which the modified metal oxide is used are in the range of 3 to 50%, based on the resin system.

The invention additionally provides toners, developers, and charge control agents which comprise the surface-modified metal oxide. Examples of such developers and toners are magnetic 1-component and 2-component toners, and also nonmagnetic toners. These toners may be composed of resins such as styrene resins and acrylic resins, and may preferably be ground to particle distributions of 1 to 100 µm, or can be resins which have been prepared in polymerization processes in dispersion or emulsion or solution or in bulk, preferably with preferably particle distributions of 1 to 100 µm. Metal oxide is preferably used to improve and control the powder flow behavior and/or to regulate and control the triboelectric charge properties of toners and developers. Toners and developers of this kind can be used with preference in electrophotographic printing and press processes, and can also be employed in direct image transfer processes.

The composition of a toner typically includes a solid resin binder which is sufficiently hard for a powder to be produced from it, preferably having a molecular weight of more than 10,000, preferably with a fraction of polymer with a molecular weight below 10,000 of less than 10% by weight, e.g., a polyester resin which may be a cocondensate of diol and carboxylic acid, carboxylic ester or carboxylic anhydride, having an acid number, for example, of 1 to 1000, preferably of 5 to 200, or a polyacrylate or a polystyrene, mixture thereof, or copolymer thereof, and having an average particle diameter of less than 20 μm, preferably less than 15 μm, more preferably less than 10 μm. Toner compositions are well known to the skilled artisan.

The toner resin may further comprise alcohols, carboxylic acids, and polycarboxylic acid, and includes colorants customary in the art, such as black carbon black, pigmentary carbon black, cyan dyes, magenta dyes, and yellow dyes.

The toner typically includes positive charge control agents: charge control additives of the nigrosine dye type, for example, or triphenylmethane dyes substituted by tertiary amines, or quaternary ammonium salts such as CTAB (cetyltrimethylammonium bromide or hexadecyltrimethylammonium bromide), or polyamines, typically in amounts of less than 5% by weight.

Optionally, negative charge control agents, for example charge control additives such as metal azo dyes, or copper phthalocyanine dyes, or metal complexes of alkylated salicylic acid derivatives or benzoic acid, particularly complexes with boron or aluminum, in the amounts required, typically less than 5% by weight, may be included.

If desired it is possible, in order to prepare magnetic toners, to add magnetic powders such as powders which can be magnetized in a magnetic field, for example ferromagnetic substances such as iron, cobalt, nickel, various magnetic alloys, or compounds such as magnetite, hematite or ferrite. Optionally it is also possible to add developers such as iron powder, glass powder, nickel powder, ferrite powder.

Metal oxide is generally used in amounts, based on a solid resin binder with an average particle diameter of 20 μm, of greater than 0.01% by weight, preferably greater than 0.1% by weight. As the average particle diameter of the binder goes down the amounts of metal oxide required are, generally speaking, greater, with the amount of metal oxide required increasing in inverse proportion to the particle diameter of the binder. In any case, however, the amount of metal oxide is preferably less than 5% by weight based on binder resin.

Further inorganic additions, such as fine and coarse silicon dioxides, including those with an average diameter of from 100 to 1000 nm, aluminum oxides such as pyrogenic aluminas, titanium dioxides such as pyrogenic, anatase or rutile, and zirconium oxides are also possible ingredients.

Waxes, such as paraffinic waxes having 10 to 500 carbon atoms, silicone waxes, olefinic waxes, waxes having an iodine number of <50, preferably <25, and a hydrolysis number of 10 to 1000, preferably 25 to 300, can be used.

The toner can be used in various development processes, such as for electrophotographic image production and reproduction, for example as magnetic brush processes, cascades processes, use of conductive and nonconductive magnetic systems, powder cloud processes, development in impression, and others.

The use of the silanes of the general formula II produces, in particular, the following advantages: high reaction yields, hence being economic and sparing of resources; a high degree of silylation with minimal use of silylating agents; a reproducible amount of functional groups as a result of mild reaction conditions; and silylation in the absence of catalysts, which for process-related reasons often have to remain in the product, and which might adversely affect the quality and performance of the end product.

All of the above symbols in the above formulae have their definitions in each case independently of one another, and mixtures of the various compounds may be used as well as individual compounds.

The following examples and comparative examples will serve to explain the invention further, but should not be construed as limiting the invention.

EXAMPLES

Example 1

At a temperature of 25° C. under $N_2$ inert gas 1.5 g of fully deionized (DI) water are added by atomization in very finely divided form to 100 g of pyrogenic hydrophilic silica having a moisture content of less than 1%, an HCl content of less than 100 ppm, and a specific surface area of 130 $m^2/g$ measured by the BET method in accordance with DIN 66131 and 66132, available under the name WACKER HDK S13 from Wacker-Chemie GmbH, Munich, D, and also, by atomization through a single-fluid nozzle at a pressure of 5 bar, 8.5 g of methacryloyloxymethyl-trimethoxysilane are added. The silica thus loaded is subsequently reacted under $N_2$ at a temperature of 25° C. for 3.0 h and then purified to remove water and MeOH in a 100 l drying cabinet at 80° C. for 1 h, providing a white hydrophobic silica powder with a homogeneous layer of silylating agent. The analytical data are set out in Table 1.

Example 2

At a temperature of 25° C. under $N_2$ inert gas 1.5 g of DI water are added by atomization in very finely divided form to 100 g of pyrogenic hydrophilic silica having a moisture content of less than 1%, an HCl content of less than 100 ppm, and a specific surface area of 130 $m^2/g$ measured by the BET method in accordance with DIN 66131 and 66132, available under the name WACKER HDK S13 from Wacker-Chemie GmbH, Munich, D, and also, by atomization through a single-fluid nozzle at a pressure of 5 bar, 10.0 g of methacryloyloxymethyl-triethoxysilane are added. The silica thus loaded is subsequently reacted under $N_2$ at a temperature of 25° C. for 3.0 h and then purified to remove water and MeOH in a 100 l drying cabinet at 80° C. for 1 h, providing a white hydrophobic silica powder with a homogeneous layer of silylating agent. The analytical data are set out in Table 1.

Example 3

At a temperature of 25° C. under $N_2$ inert gas 1.5 g of DI water are added by atomization in very finely divided form to 100 g of pyrogenic hydrophilic silica, having a moisture content of less than 1%, an HCl content of less than 100 ppm, and a specific surface area of 130 $m^2/g$ measured by the BET method in accordance with DIN 66131 and 66132, available under the name WACKER HDK S13 from Wacker-Chemie GmbH, Munich, D, and also, by atomization through a single-fluid nozzle at a pressure of 5 bar, 5.0 g of aminomethyldimethylmethoxysilane are added. The silica thus loaded is subsequently reacted under $N_2$ at a temperature of 25° C. for 3.0 h and then purified to remove water and MeOH in a 100 l drying cabinet at 80° C. for 1 h, providing a white hydrophobic silica powder with a homogeneous layer of silylating agent. The analytical data are set out in Table 1.

Example 4

At a temperature of 25° C. under $N_2$ inert gas 1.5 g of DI water are added by atomization in very finely divided form to 100 g of pyrogenic hydrophilic silica having a moisture content of less than 1%, an HCl content of less than 100 ppm, and a specific surface area of 130 m²/g measured by the BET method in accordance with DIN 66131 and 66132, available under the name WACKER HDK S13 from Wacker-Chemie GmbH, Munich, D, and also, by atomization through a single-fluid nozzle at a pressure of 5 bar, 6.5 g of aminomethyltrimethoxysilane are added. The silica thus loaded is subsequently reacted under $N_2$ at a temperature of 25° C. for 3.0 h and then purified to remove water and MeOH in a 100 l drying cabinet at 80° C. for 1 h, providing a white hydrophobic silica powder with a homogeneous layer of silylating agent. The analytical data are set out in Table 1.

Example 5

At a temperature of 25° C. under $N_2$ inert gas by atomization through a single-fluid nozzle at a pressure of 5 bar, 13.5 g of diethylaminomethyldiethoxy-methylsilane are added to 100 g of pyrogenic hydrophilic silica having a moisture content of less than 1%, an HCl content of less than 100 ppm, and a specific surface area of 200 m²/g measured by the BET method in accordance with DIN 66131 and 66132, available under the name WACKER HDK N20 from Wacker-Chemie GmbH, Munich, D. The silica thus loaded is subsequently reacted under $N_2$ at a temperature of 25° C. for 3.0 h and then purified in a 100 l drying cabinet at 80° C. for 1 h, providing a white hydrophobic silica powder with a homogeneous layer of silylating agent. The analytical data are set out in Table 1.

Example 6

In a continuous apparatus at a temperature of 30° C. under $N_2$ inert gas, 50 g/h of DI water in very finely divided form are introduced through a nozzle to a mass flow of 1000 g/h of pyrogenic hydrophilic silica, having a moisture content of less than 1%, an HCl content of less than 100 ppm, and a specific surface area of 200 m²/g measured by the BET method in accordance with DIN 66131 and 66132, available under the name WACKER HDK N20 from Wacker-Chemie GmbH, Munich, D, 180 g/h of an OH-terminal polydimethylsiloxane having a viscosity at 25° C. of 40 mPas and an OH content of 4% by weight, and 130 g/h of methacryloyloxymethyltrimethoxysilane in liquid, very finely divided form are added by atomization through a single-fluid nozzle at a pressure of 10 bar. The silica thus loaded is further fluidized by means of stirring, with a residence time of 2 hours, at a temperature of 30° C., and is then reacted in a reactor at 100° C. with a residence time of 4 hours, providing a white hydrophobic silica powder with a homogeneous layer of silylating agent. The analytical data are set out in Table 1.

Example 7

In a continuous apparatus at a temperature of 30° C. under $N_2$ inert gas, 50 g/h of DI water in very finely divided form are introduced through a nozzle to a mass flow of 1000 g/h of pyrogenic hydrophilic silica having a moisture content of less than 1%, an HCl content of less than 100 ppm, and a specific surface area of 200 m²/g measured by the BET method in accordance with DIN 66131 and 66132, available under the name WACKER HDK N20 from Wacker-Chemie GmbH, Munich, D, 100 g/h of chloromethyltrimethoxysilane in liquid, very finely divided form are added by atomization through a single-fluid nozzle of pressure of 10 bar. The silica thus loaded is further fluidized by means of stirring, with a residence time of 3 hours at a temperature of 30° C., and is then purified to remove water and MeOH in a reactor at 120° C. with a residence time of 1 hour, providing a white hydrophobic silica powder with a homogeneous layer of silylating agent. The analytical data are set out in Table 1.

Comparative Example C1 (not inventive)

At a temperature of 25° C. under $N_2$ inert gas, 5.0 g of ammonia water are added by atomization in very finely divided form to 100 g of hydrophilic silica having a moisture content of less than 1%, an HCl content of <100 ppm, and a specific surface area of 200 m²/g measured by the BET method in accordance with DIN 66131 and 66132, available under the name WACKER HDK N20 from Wacker-Chemie GmbH, Munich, D, and also, by atomization through a single-fluid nozzle at a pressure of 5 bar, 16.0 g of methacryloyloxypropyl-trimethoxysilane available under the name Silan GF31 from Wacker-Chemie GmbH, Munich, D are added. The silica thus loaded is subsequently reacted at a temperature of 150° C. for 4.0 h in a 100 l drying cabinet, providing a white hydrophobic silica powder with a homogeneous layer of silylating agent. The analytical data are set out in Table 1.

Example 8

At a temperature of 25° C. under $N_2$ inert gas, 1.2 g of fully deionized (DI) water are added by atomization in very finely divided form to 100 g of pyrogenic alumina having a specific surface area of 100 m²/g measured by the BET method in accordance with DIN 66131 and 66132, available under the name Degussa Aluminium Oxide C from Degussa, Hanau, D, and also, by atomization through a single-fluid nozzle of a pressure of 5 bar, 6.3 g of methacryloyloxymethyl-trimethoxysilane are added. The alumina thus loaded is subsequently reacted under $N_2$ at a temperature of 25° C. for 3.0 h and then purified to remove water and MeOH in a 100 l drying cabinet at 80° C. for 1 h. This gives a white hydrophobic alumina powder with a homogeneous layer of silylating agent.

The analytical data are set out in Table 1.

TABLE 1

| Example | % C | Bet [m²/g] | pH | Si-AAS [ppm/100 g metal oxide] |
|---|---|---|---|---|
| 1 | 2.3 | 85 | 5.6 | 151 |
| 2 | 2.9 | 93 | 5.8 | 490 |
| 3 | 1.3 | 83 | 10.2 | <12 |
| 4 | 1.15 | 80 | 10.2 | <12 |
| 5 | 3.2 | 118 | 9.8 | <12 |
| 6 | 8.05 | 109 | 5.3 | 1315 |
| 7 | 1.08 | 123 | 5.1 | 273 |
| 8 | 1.7 | 68 | 5.5 | 552 |
| C1 | 5.14 | 114 | 5.5 | 527 |

Description of Analytical Methods
 1. Carbon content (% C)
  Elemental analysis for carbon; combustion of the sample at >1000° C. in a stream of $O_2$, detection and quantification of the resulting $CO_2$ by IR; instrument: LECO 244

2. BET
   Measured by the BET method in accordance with DIN 66131 and 66132
3. pH
   4% (by weight) suspension of the metal oxide in saturated aqueous sodium chloride solution: methanol=50:50
4. Si-AAS
   Extraction of metal oxide with THF and determination of the Si content of the extract filtrate by means of Si-AAS for quantitative determination of the soluble constituents after surface modification Example 9

Charge Behavior of the Silica 50 g portions of a ferrite carrier having an average particle diameter of 80 μm are mixed with 0.5 g portions of the silica from Examples 3 and 4 at RT (room temperature) by shaking in a 100 ml PE (polyethylene) vessel for 15 minutes. Prior to measurement, these mixtures are activated on a roller bed for 5 minutes at 64 rpm in a sealed 100 ml PE vessel. Using a "hard-blow-off cell" employing approximately 3 g of silica, capacity 10 nF, 45 μm screen, air flow 1 l/min, air pressure 2.4 kPa, measurement time 90 s, (EPPING GmbH, D-85375 Neufahrn) the triboelectric charging behavior of the silica is measured as the ratio of silica charge to silica mass (q/m). The results are presented in Table 2

TABLE 2

| Example | Charge behavior q/m against ferrite [μC/g] |
|---|---|
| Carrier + Example 3 | +280 |
| Carrier + Example 4 | +130 |

Example 10

Flow and Charge Behavior of Silica Toner 100 g of a silica-free magnetic 1-component dry toner of the negatively charging "crushed" type, based on styrene-methacrylate copolymer, with an average particle size of 14 μm, obtainable, for example, from IMEX, Japan are mixed with 0.4 g of a silica according to Examples 3-4 in a tumble mixer e.g. Turbular™ at RT for 1 hour. After a toner exposure time of 20 minutes, corresponding to the loading experience after 1000 copying operations, the charging (charge per mass) of the ready-produced silica toner and the flow behavior (mass flow) of the ready-produced silica toner to the developing roller are measured in a "q/m mono" electrometer/flow tester (EPPING GmbH, D-85375 Neufahrn). The results are presented in Table 3.

TABLE 3

| Example | Toner charge [μC/g] | Flow behavior [mg] |
|---|---|---|
| Silica-free toner | +0.50 | 2 |
| Toner + Example 3 | +3.0 | 48 |
| Toner + Example 4 | +1.8 | 27 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for preparing a metal oxide having groups of the formula I $$-O_{1+n}-SiR^1_{2-n}-CH_2-Y \qquad (I)$$

comprising reacting solid having OH groups on a surface thereof with at least one silane of the formula II $$RO_{1+n}-SiR^1_{2-n}-CH_2-Y \qquad (II)$$

where
   R is a C—O bonded $C_1$-$C_{15}$ hydrocarbon radical,
   $R^1$ is a hydrogen atom or an Si—C bonded $C_1$-$C_{20}$ hydrocarbon radical unsubstituted or substituted by —CN, —NCO, —NR$^x$$_2$, —COOH, —COOR$^x$, -halo, -acryloyl, -epoxy, —SH, —OH or —CONR$^x$$_2$, or a $C_1$-$C_{15}$ hydrocarbon radical in which one or more nonadjacent methylene units are replaced by a group —O—, —CO—, —COO—, —OCO—, or —OCOO—, —S— or —NR$^x$— and/or in which one or more nonadjacent methine units are optionally replaced by a group —N=, —N= or —P=, each $R^1$ being identical or different,
   Y is a functional group —NR$^x$$_2$, —OC(O)C(R)=CH$_2$, -halo, —NCO, —NH—C(O)—OR, glycidoxy, —SH, or $(R^1O)_2(O)P$—, wherein R is H or a $C_{1-15}$ hydrocarbon radical,
   $R^x$ is a hydrogen atom, a $C_1$-$C_{15}$ hydrocarbon radical or an aryl radical, each $R^x$ being identical or different,
   and n is 0, 1 or 2,
wherein the silane (II) is sprayed onto the metal oxide in the form of an atomized liquid.

2. A process for preparing a metal oxide having groups of the formula I $$-O_{1+n}-SiR^1_{2-n}-CH_2-Y \qquad (I)$$

comprising reacting solid having OH groups on a surface thereof with at least one silane of the formula II $$RO_{1+n}-SiR^1_{2-n}-CH_2-Y \qquad (II)$$

where
   R is a C—O bonded $C_1$-$C_{15}$ hydrocarbon radical,
   $R^1$ is a hydrogen atom or an Si—C bonded $C_1$-$C_{20}$ hydrocarbon radical unsubstituted or substituted by —CN, —NCO, —NR$^x$$_2$, —COOH, —COOR$^x$, -halo, -acryloyl, -epoxy, —SH, —OH or —CONR$^x$$_2$, or a $C_1$-$C_{15}$ hydrocarbon radical in which one or more nonadjacent methylene units are replaced by a group —O—, —CO—, —COO—, —OCO—, or —OCOO—, —S— or —NR$^x$— and/or in which one or more nonadjacent methine units are optionally replaced by a group —N=, —N= or —P=, each $R^1$ being identical or different,
   Y is a functional group —NR$^x$$_2$, —OC(O)C(R)=CH$_2$, -halo, —NCO, —NH—C(O)—OR, glycidoxy, —SH, or $(R^1O)_2(O)P$—, wherein R is H or a $C_{1-15}$ hydrocarbon radical,
   $R^x$ is a hydrogen atom, a $C_1$-$C_{15}$ hydrocarbon radical or an aryl radical, each $R^x$ being identical or different,
   and n is 0, 1 or 2,
wherein the silanes of the formula II are employed together with at least one organosiloxane composed of one or more units of the formulae $(R^3{}_3SiO_{1/2})$, $(R^3{}_2SiO_{2/2})$, and $(R^3SiO_{3/2})$, the number of these units in an organosiloxane being at least 2, wherein $R^3$ is an optionally mono- or polyunsaturated, monovalent, optionally halogenated hydrocarbon radical having 1 to 18 carbon atoms, halogen, a nitrogen radical, $OR^4$, $OCOR^4$, or $O(CH2)_xOR^4$, where $R^4$ is hydrogen or a monovalent hydrocarbon radical having 1 to 18 carbon atoms, and the radicals $R^3$ may be identical or different.

3. The process of claim 1, wherein Y is an amino, mercapto, isocyanato, phosphonato, or carbamato group.

4. A process for preparing a metal oxide having groups of the formula I $$—O_{1+n}—SiR^1{}_{2-n}—CH_2—Y \quad (I)$$

comprising reacting solid having OH groups on a surface thereof with at least one silane of the formula II $$RO_{1+n}—SiR^1{}_{2-n}—CH_2—Y \quad (II)$$

where

R is a C—O bonded $C_1$-$C_{15}$ hydrocarbon radical, $R^1$ is a hydrogen atom or an Si—C bonded $C_1$-$C_{20}$ hydrocarbon radical unsubstituted or substituted by —CN, —NCO, —$NR^x{}_2$, —COOH, —$COOR^x$, -halo, -acryloyl, -epoxy, —SH, —OH or —$CONR^x{}_2$, or a $C_1$-$C_{15}$ hydrocarbon radical in which one or more nonadjacent methylene units are replaced by a group —O—, —CO—, —COO—, —OCO—, or —OCOO—, —S— or —$NR^x$— and/or in which one or more nonadjacent methine units are optionally replaced by a group —N═, —N══ or —P═, each $R^1$ being identical or different, Y is a functional group —$NR^x{}_2$, —OC(O)C(R)═$CH_2$, -halo, —NCO, —NH—C(O)—OR, glycidoxy, —SH, or $(R^1O)_2(O)P$—, wherein R is H or a $C_{1-15}$ hydrocarbon radical, $R^x$ is a hydrogen atom, a $C_1$-$C_{15}$ hydrocarbon radical or an aryl radical, each $R^x$ being identical or different, and n is 0, 1 or 2, wherein the silane of the formula II is a monoalkoxysilane.

5. The process as claimed of claim 1, wherein Y is a halo, acrylate, alkylacrylate or glycidyloxy group.

6. The process of claim 5, wherein the silane of the formula II is a monoalkoxysilane RO—$SiR^1{}_2$—$CH_2$—Y wherein the C—O bonded hydrocarbon radicals R are individually selected from the group consisting of methyl radicals and acetyl radicals.

7. The process of claim 5, wherein the silane of the formula II is a dialkoxysilane $(RO)_2$—$SiR^1$—$CH_2$—Y wherein the C—O bonded hydrocarbon radical R is independently selected from the group consisting of methyl radicals and acetyl radicals.

8. The process of claim 5, wherein the silane of the formula II is a trialkoxysilane $(RO)_3Si$—$CH_2$—Y wherein the C—O bonded hydrocarbon radical R is independently selected from the group consisting of methyl radicals and acetyl radicals.

9. The process of claim 1, wherein the solid is silicon dioxide.

10. A metal oxide with a modified surface, prepared by the process of claim 1.

11. The metal oxide of claim 10, comprising silica.

12. The metal oxide of claim 10, wherein the group of the formula I is a mono-, di- or trisiloxy radical of one or more of the formulae —O—$SiR^1{}_2$—$CH_2$—Y, $(—O)_2SiR^1$—$CH_2$—Y, and $(—O)_3Si$—$CH_2$—Y, wherein Y is an amino, mercapto, isocyanato, phosphonato, or carbamato group.

13. The metal oxide of claim 12, wherein the group of the formula I is a monosiloxy radical —O—$SiR^1{}_2$—$CH_2$—Y, wherein Y is an amino, mercapto, isocyanato, phosphonato, or carbamato group.

14. The metal oxide of claim 10, wherein the group of the formula I is a mono-, di- or trisiloxy radical of the formula —O—$SiR^1{}_2$—$CH_2$—Y, $(—O)_2SiR^1$—$CH_2$—Y, and $(—O)_3Si$—$CH_2$—Y, wherein Y is a halo, acrylate, alkylacrylate, or glycidyloxy group.

15. The metal oxide of claim 14, wherein the group of the formula I is a trisiloxy radical $(—O)_3$—$SiR^1{}_2$—$CH_2$—Y, wherein Y is a halo, acrylate, alkylacrylate, or glycidyloxy group.

\* \* \* \* \*